US008779228B2

(12) United States Patent
Heidemann et al.

(10) Patent No.: US 8,779,228 B2
(45) Date of Patent: Jul. 15, 2014

(54) OLIGOMERISATION OF OLEFINS

(75) Inventors: Thomas Heidemann, Viernheim (DE);
Armin Ulonska, Niederkirchen (DE)

(73) Assignee: BASF SE, Ludwigshafen (DE)

( * ) Notice: Subject to any disclaimer, the term of this patent is extended or adjusted under 35 U.S.C. 154(b) by 455 days.

(21) Appl. No.: 13/128,895

(22) PCT Filed: Nov. 18, 2009

(86) PCT No.: PCT/EP2009/065367
§ 371 (c)(1),
(2), (4) Date: Jul. 14, 2011

(87) PCT Pub. No.: WO2010/057905
PCT Pub. Date: May 27, 2010

(65) Prior Publication Data
US 2011/0301398 A1 Dec. 8, 2011

(30) Foreign Application Priority Data
Nov. 19, 2008 (EP) .................. 08169453

(51) Int. Cl.
*C07C 2/10* (2006.01)
(52) U.S. Cl.
USPC ........... 585/531; 585/510; 585/520; 585/530; 585/906; 502/34; 502/337; 502/514
(58) Field of Classification Search
USPC ................ 585/502, 510, 520, 530, 531, 906; 502/337, 34, 514
See application file for complete search history.

(56) References Cited

U.S. PATENT DOCUMENTS

| 3,959,400 | A | * | 5/1976 | Lucki | 585/515 |
| 4,511,750 | A | * | 4/1985 | Miller | 585/526 |
| 4,717,782 | A | * | 1/1988 | Garwood et al. | 585/531 |
| 4,740,645 | A | | 4/1988 | Garwood et al. | |
| 5,550,304 | A | | 8/1996 | Chauvin et al. | |
| 5,817,589 | A | * | 10/1998 | de Agudelo et al. | 502/53 |
| 5,849,972 | A | * | 12/1998 | Vicari et al. | 585/531 |
| 6,737,555 | B1 | | 5/2004 | Maas et al. | |
| 2010/0016646 | A1 | | 1/2010 | Koenigsmann et al. | |
| 2010/0048959 | A1 | | 2/2010 | Sigl et al. | |
| 2010/0174117 | A1 | | 7/2010 | Heidemann et al. | |
| 2010/0286458 | A1 | | 11/2010 | Iselborn et al. | |
| 2011/0009671 | A1 | | 1/2011 | Sigl et al. | |
| 2011/0124933 | A1 | | 5/2011 | Kiesslich et al. | |

FOREIGN PATENT DOCUMENTS

| DE | 43 39 713 | 5/1995 |
| DE | 199 15 357 | 10/2000 |
| DE | 10 2005 060376 | 6/2007 |
| JP | 2003 326169 | 11/2003 |
| WO | 99 25668 | 5/1999 |
| WO | 00 53546 | 9/2000 |

OTHER PUBLICATIONS

Hardenburger, et al., "Nitrogen" in Kirk-Othmer Encyclopedia of Chemical Technology, John Wiley & Sons, 2001, available on-line May 13, 2005.*
U.S. Appl. No. 13/186,592, filed Jul. 20, 2011, Schneider, et al.
Chauvel, A. and Lefebvre, G. "Petrochemical Processes: Technical and Economic Characteristics." Editions Technip. pp. 183-187 (1989).
Asinger, F. "Die Petrolchemische Industrie." Akademie-Verlag. pp. 278-299 (1971).
O'Connor, C.T. and Kojima, M. "Alkene Oligomerization." Catalysis Today. pp. 329-349 (1990).
International Search Report issued May 10, 2010 in PCT/EP09/065367 filed Nov. 18, 2009.
U.S. Appl. No. 13/500,966, filed Apr. 9, 2012, Tsou, et al.

* cited by examiner

*Primary Examiner* — In Suk Bullock
*Assistant Examiner* — Bradley Etherton
(74) *Attorney, Agent, or Firm* — Oblon, Spivak, McClelland, Maier & Neustadt, L.L.P.

(57) ABSTRACT

Olefins are oligomerized by bringing at least one $C_2$ to $C_8$-olefin into contact with a nickel-containing heterogeneous catalyst. The catalyst is conditioned before contact with the olefin by passing an inert gas flow over the same, until the inert gas flow has a water content of less than 1000 ppm. Selectivity for the production of higher oligomers, in particular trimers relative to the formation of dimers is increased by the pretreatment.

12 Claims, No Drawings

OLIGOMERISATION OF OLEFINS

The present invention relates to a process for oligomerizing $C_2$-$C_8$-olefins over a nickel-comprising heterogeneous catalyst.

Olefins having from 2 to 8 carbon atoms or mixtures thereof are available in large quantities both from FCC (Fluidized Catalyst Cracking) plants and from steam crackers. The use of $C_4$ fraction, i.e. a mixture comprising essentially butenes and butanes, if appropriate after removal of the isobutene, for the preparation of oligomers, in particular octenes and dodecenes, is known. Both the octenes and the dodecenes can, after hydroformylation and subsequent hydrogenation to the corresponding alcohols, be used, for example, for preparing plasticizers or surfactants.

The oligomerization is carried out industrially under either homogeneous or heterogeneous catalysis. The homogeneously catalyzed process has the disadvantage that the catalyst has to be separated from the reaction mixture. This separation step results in waste streams which have to be subjected to a complicated work-up. In addition, the homogeneous catalyst cannot be regenerated.

The disadvantages described do not occur in the heterogeneously catalyzed olefin oligomerization. The most important heterogeneously catalyzed olefin oligomerization processes employed in the industry are described, for example, in A. Chauvel and G. Lefebvre, Petrochemical Process, Edition Technip (1989), pp. 183-187 and F. Asinger, Die petrolchemische Industrie, Akademie-Verlag (1971), pp. 278-299.

DE-43 39 713 discloses a process for oligomerizing unbranched $C_2$-$C_8$-olefins over a fixed-bed catalyst at superatmospheric pressure and elevated temperature, in which the catalyst comprises, as significant active constituents, from 10 to 70% by weight of nickel oxide, from 5 to 30% by weight of titanium dioxide and/or zirconium dioxide, from 0 to 20% by weight of aluminum oxide and silicon oxide as balance. The oligomerization of butenes can be carried out with very good selectivity to linear products by this process. Preferred process conditions are described in WO 99/25668 and WO 00/53546.

DE-43 39 713 recommends subjecting the freshly prepared catalyst to conditioning in a stream of dry nitrogen, e.g. at atmospheric pressure and temperatures of from 200 to 500° C., before use in order to remove water still comprised from the catalyst. The publication does not indicate a residual water content which remains in the catalyst after conditioning. It has now been found that the selectivity of the catalyst in respect of formation of dimers and trimers can be influenced by the conditions under which the catalyst is conditioned before contact with the olefin.

It is an object of the present invention to provide a process for oligomerizing $C_2$-$C_8$-olefins in which the selectivity to the formation of higher oligomers, in particular trimers, compared to the formation of dimers is increased.

The invention accordingly provides a process for oligomerizing olefins by bringing at least one $C_2$-$C_8$-olefin into contact with a nickel-comprising heterogeneous catalyst, wherein the catalyst is conditioned by passing an inert gas stream over it until the outflowing inert gas stream has a water content of less than 1000 ppm, preferably less than 500 ppm, before contact with the olefin.

Since the direct determination of the residual water content of the catalyst can be achieved only with difficulty during and after conditioning, the water content of the outflowing inert gas stream serves as a measure of the progress of conditioning in the present invention. This mode of operation allows simple monitoring and control of the conditioning conditions.

The process of the invention allows the preparation of olefin oligomers, with the weight ratio of the olefin trimers and higher oligomers formed to the olefin dimers being, for example, more than 0.2

The heterogeneous nickel-comprising catalysts which can be used can have various structures. It is possible to use catalysts known per se, as are described in C. T. O'Connor et al., Catalysis Today, Vol. 6 (1990), pp. 336-338. In particular, supported nickel catalysts are used. The support materials can be, for example, silica, alumina, aluminosilicates, aluminosilicates having sheet structures and zeolites such as mordenite, faujasite, zeolite X, zeolite Y and ZSM-5, zirconium oxide which has been treated with acids or sulfated titanium dioxide. Precipitated catalysts which can be obtained by mixing of aqueous solutions of nickel salts and silicates, e.g. sodium silicate with nickel nitrate, and, if appropriate, aluminum salts such as aluminum nitrate, and calcination are particularly useful. Furthermore, it is possible to use catalysts which are obtained by incorporation of $Ni^{2+}$ ions into natural or synthetic sheet silicates such as montmorillonites by ion exchange. Suitable catalysts can also be obtained by impregnation of silica, alumina or aluminosilicates with aqueous solutions of soluble nickel salts such as nickel nitrate, nickel sulfate or nickel chloride and subsequent calcination.

Catalysts comprising nickel oxide are preferred. Particular preference is given to catalysts comprising essentially NiO, $SiO_2$, $TiO_2$ and/or $ZrO_2$ and, if appropriate, $Al_2O_3$. Such catalysts are especially preferred when the process of the invention is employed for the oligomerization of butenes or pentenes. They give predominantly linear products. Greatest preference is given to a catalyst which comprises, as significant active constituents, from 10 to 70% by weight of nickel oxide, from 5 to 30% by weight of titanium dioxide and/or zirconium dioxide, from 0 to 20% by weight of aluminum oxide and silicon dioxide as balance. Such a catalyst can be obtained by precipitation of the catalyst composition at pH 5-9 by addition of an aqueous solution comprising nickel nitrate to an alkali metal water glass solution comprising titanium dioxide and/or zirconium dioxide, filtration, drying and heating at from 350 to 650° C. Details of the preparation of these catalysts may be found in DE-43 39 713. The disclosure of this document and the prior art cited therein are fully incorporated by reference.

The catalyst is preferably present in the form of shaped bodies, e.g. in the form of pellets, e.g. having a diameter of from 2 to 6 mm and a height of from 3 to 5 mm, rings having, for example, an external diameter of from 5 to 7 mm, a height of from 2 to 5 mm and a diameter of the central hole of from 2 to 3 mm or extrudates of various lengths having a diameter of, for example, from 1.5 to 5 mm. Such shapes are obtained in a manner known per se by tableting or extrusion, usually using a tableting aid such as graphite or stearic acid.

To carry out conditioning, the catalyst is heated to a temperature of greater than 100° C., preferably from 100 to 500° C., e.g. from 150 to 500° C., in the presence of an inert gas. Heating can be carried out for a period ranging from a few hours to a number of days, e.g. from 6 to 150 hours, preferably from 30 to 72 hours. The inert gas, which can be under atmospheric pressure or superatmospheric pressure, e.g. a pressure of from 0.9 to 1.5 bar, is preferably passed through a bed of catalyst.

To heat the catalyst bed, it is possible to use, for example, a heating facility provided in the reactor wall when conditioning is carried out in situ in the oligomerization reactor.

Suitable inert gases are gases which experience essentially no chemical change over the catalyst at the conditioning temperature and undergo essentially no chemical or physical interaction with the catalyst. Examples of suitable gases are nitrogen, argon or neon, among which nitrogen is most preferred. In general, the inflowing inert gas stream has a water content of less than 250 ppm, in particular less than 100 ppm.

In preferred embodiments, from 10 to 1000 standard l/h, in particular from 50 to 500 standard l/h, of inert gas per l of catalyst bed are passed over the catalyst. For the purposes of the present invention, a standard liter (standard l) is a quantity of gas which occupies a volume of 1 l under standard conditions (20° C., 1013 hPa).

According to the invention, the water content of the outflowing inert gas stream is measured; the measurement can be carried out periodically or continuously. A suitable method of determining the water content of the outflowing inert gas stream is, for example, a capacitative moisture sensor, e.g. the Minicap 2 moisture sensor from GE Parametrics. Before the measurement, the inert gas stream can be brought to a suitable measurement temperature, e.g. about 60° C.

After a desired water content has been achieved in the outflowing inert gas stream, the catalyst bed is preferably allowed to cool in the inert gas stream, e.g. to below 40° C.

The conditioning and the oligomerization can be carried out separately from one another in space and/or time. This situation normally occurs, for example, when conditioning is carried out in temporal and/or spatial relationship with the preparation of the catalyst. However, it is generally preferred that the conditioning and the oligomerization are carried out in the same reactor. Preference is also given to carrying out the conditioning of the catalyst immediately before commencement of the oligomerization.

Before the actual oligomerization, the catalyst can be subjected to a pretreatment in which it is brought into contact with a hydrocarbon mixture which is lower in olefin than the actual product feed mixture, as described in WO 00/059849. The contact of the catalyst with hydrocarbons is generally accompanied by a temperature increase due to the enthalpy of adsorption which is liberated. If this evolution of heat occurs simultaneously with the exothermic oligomerization reaction, the catalyst may be exposed to high temperatures which adversely affect the activity and life of the catalyst. However, if the catalyst is firstly brought into contact with a low-olefin hydrocarbon mixture in which little if any oligomerizable olefins are present, the heat of adsorption can be removed without problems.

To carry out the oligomerization, the catalyst is brought into contact with at least one $C_2$-$C_8$-olefin such as ethylene, propylene, n-butene, n-pentene and n-hexene. The olefin (mixture) preferably comprises n-butene and/or n-pentene.

The industrially available olefin-comprising hydrocarbon streams which are suitable for carrying out the process of the invention are generally mixtures. Hydrocarbon mixtures having a content of $C_2$-$C_8$-olefins of from 50 to 100% by weight, preferably from 60 to 100% by weight, are suitable. The olefin component is generally essentially one olefin such as propylene or a mixture of olefins having the same number of carbon atoms, e.g. isomeric butenes. The hydrocarbon mixture can comprise not only $C_2$-$C_8$-olefins but also a proportion of inerts which are not capable of oligomerization. These inerts can comprise, for example, saturated hydrocarbons such as alkanes, e.g. propane, butane, pentane, hexane, heptane, octane, nonane, decane, undecane and/or dodecane and/or cycloalkanes. In general, the saturated hydrocarbons have the same number of carbon atoms as the olefin or one carbon atom more or fewer than the olefin.

A preferred hydrocarbon mixture comprises from 50 to 100% by weight, preferably from 60 to 90% by weight, of butenes and from 0 to 50% by weight, preferably from 10 to 40% by weight, of butanes. The butene fraction preferably comprises less than 5% by weight, in particular less than 3% by weight, of isobutene (based on the butene fraction). The butene fraction generally has the following composition (in each case based on the butene fraction):

| 1-butene | from 1 to 50% by weight, |
| cis-2-butene | from 1 to 50% by weight, |
| trans-2-butene | from 1 to 99% by weight. |
| isobutene | from 1 to 5% by weight. |

A particularly preferred feed is raffinate II which is an isobutene-depleted $C_4$ fraction from an FCC plant or a steam cracker. Raffinate II has the following typical composition:

| i-, n-butane | 26% by weight, |
| i-butene | 1% by weight |
| 1-butene | 26% by weight, |
| trans-2-butene | 31% by weight, |
| cis-2-butene | 16% by weight. |

If diolefins or alkynes are present in the hydrocarbon mixture, these are removed to a level of less than 10 ppm by weight, preferably less than 5 ppm by weight, in particular less than 1 ppm by weight, before the oligomerization. They are preferably removed by selective hydrogenation, e.g. as described in EP-81041 and DE-1568542.

The industrially available hydrocarbon mixtures which are suitable as hydrocarbon mixture for the purposes of the present invention often comprise compounds which act as catalyst poisons and deactivate the oligomerization catalyst. These include oxygen-comprising compounds such as alcohols, aldehydes, ketones and ethers and also nitrogen-comprising, sulfur-comprising and halogen-comprising compounds. The presence of such catalyst poisons would lead to an undesirable reduction in the catalyst activity. It is advantageous for oxygen-comprising compounds such as alcohols, aldehydes, ketones or ethers to be largely removed from the hydrocarbon mixture. The concentration of oxygen-comprising, sulfur-comprising, nitrogen-comprising and halogen-comprising compounds in the hydrocarbon mixture is preferably less than 1 ppm by weight, in particular less than 0.5 ppm by weight.

According to a preferred aspect of the invention, the hydrocarbon mixture is therefore passed over an adsorbent to remove catalyst poisons before being brought into contact with the catalyst. Suitable adsorbents are molecular sieves, preferably ones having a pore diameter of from >4 Å to 15 Å. As molecular sieves, it is possible to use crystalline, natural aluminum silicates, e.g. sheet silicates, and also synthetic molecular sieves. Commercial molecular sieves such as those from Bayer AG, Dow, Union Carbide, Laporte or Mobil are also suitable. These molecular sieves can be, for example, zeolites of the A, X and Y type. Furthermore, synthetic molecular sieves comprising not only silicon and aluminum as main constituents but also other atoms as secondary constituents are also suitable. These can, for example, be incorporated into the zeolite by ion exchange with the exchangeable cations. Exchange with rare earths such as gallium, indium or lanthanum or with nickel, cobalt, copper, zinc or silver may be mentioned by way of example here.

Furthermore, synthetic zeolites in which other atoms such as boron or phosphorus have been incorporated into the lattice by coprecipitation can also be used.

Further suitable adsorbents are, for example, aluminum oxides, aluminum phosphates, silicon dioxides, kieselguhr, titanium dioxides, zirconium dioxides, polymeric adsorbents and mixtures thereof. The hydrocarbon mixture is advantageously passed over the adsorbent in a fixed bed or a moving bed. The hydrocarbon mixture can be present in the gaseous or liquid states, preferably in the liquid state, during passage over the adsorbent.

The oligomerization is preferably carried out at temperatures of from 20 to 300° C., preferably from 30 to 280° C., in particular from 30 to 140° C. and particularly preferably from 40 to 130° C. It is preferably carried out at a pressure of from 1 to 100 bar, preferably from 10 to 300 bar, in particular from 15 to 100 bar and particularly preferably from 20 to 80 bar. The pressure is advantageously set so that the hydrocarbon mixture is present in the liquid or supercritical state at the temperature selected.

Suitable, if appropriate pressure-rated reaction apparatuses for the contacting of the hydrocarbon mixture with the heterogeneous catalyst are known to those skilled in the art. They include the generally customary reactors for gas/solid reactions or liquid/solid reactions. Examples of suitable reactors are shell-and-tube reactors or shaft ovens. Owing to the lower capital costs, shaft ovens are preferred. The oligomerization process of the invention can be carried out in a single reactor, with the oligomerization catalyst being able to be arranged in a single fixed bed or a plurality of fixed beds in the reactor. As an alternative, the process of the invention can be carried out using a reactor cascade made up of a plurality of, preferably two, reactors connected in series, with the oligomerization of the olefins in the reaction mixture being carried out only to a partial conversion on passing through the reactor or reactors preceding the last reactor of the cascade and the desired final conversion being achieved only when the reaction mixture passes through the last reactor of the cascade. The oligomerization catalyst can be arranged in a single catalyst bed or in a plurality of catalyst beds in the individual reactors of the reactor cascade. Furthermore, different reaction conditions in respect of pressure and/or temperature within the abovementioned pressure and temperature ranges can be set in the individual reactors of the reactor cascade. In addition, it is possible to use different oligomerization catalysts in the individual reactors of the cascade, although the use of the same catalyst in all reactors of the cascade is preferred. The preferred reactor is generally a vertical cylindrical tube which is charged with the catalyst and through which the hydrocarbon mixture flows, for example, from the top downward.

After leaving the reactor or the last reactor of a cascade, the oligomers formed are separated off from the unreacted olefins and saturated hydrocarbons in the reactor discharge. The oligomers formed can be purified in a subsequent vacuum fractionation step.

In a preferred embodiment, the reactor discharge which has been freed of the oligomers formed and comprises essentially unreacted olefins and saturated hydrocarbons is recirculated in its entirety or in part. Preference is given to choosing the recycled ratio so that the concentration of oligomers in the reaction mixture does not exceed 35% by weight, preferably 20% by weight, based on the hydrocarbon reaction mixture, at any point in the reactor (or the reactor cascade).

The operating phase can advantageously be carried out adiabatically. The oligomerization reaction generally proceeds exothermically. The reaction mixture therefore experiences a temperature increase while flowing through the catalyst bed. For the purposes of the present invention, the term adiabatic reaction conditions refers, in contrast to isothermal reaction conditions in which the heat evolved in an exothermic reaction is removed by cooling by means of cooling or thermostating facilities and the temperature is thus kept constant, i.e. isothermal, in the reactor, to a mode of operation in which the heat liberated in an exothermic reaction is taken up by the reaction mixture in the reactor and no cooling by means of cooling facilities is employed. It goes without saying that a negligibly small part of the heat liberated in the exothermic reaction is unavoidably taken up by the reactor body and is given off into the environment by means of thermal conduction and radiation. In the industrial sense, adiabatic reaction conditions or an adiabatic mode of operation is therefore reaction conditions or a mode of operation in the case of which the entire heat of reaction, apart from the part of the heat of reaction which is given off into the environment by natural thermal conduction and radiation from the reactor, is taken up by the reaction mixture and discharged from the reactor with the latter. There are two fundamental possibilities for controlling the reaction temperature. Since in the case of the present oligomerization process the exothermic reaction occurs as a result of contact of the olefins with the catalyst and heat is therefore liberated only in the region of the catalyst bed, the temperature in the reactor can be controlled by adjusting the concentration of olefin in the inflowing hydrocarbon mixture. This is in turn advantageously regulated by the recirculation of the unreacted olefins and saturated hydrocarbons separated off from the oligomeric product back into the oligomerization reactor. Since the stream recirculated to the oligomerization reactor has a lower content of reactive olefins and a higher content of saturated hydrocarbons which are inert under the reaction conditions compared to the freshly introduced hydrocarbon feed stream, the recycle stream added to the feed stream effects only dilution of the olefin content. The reactor temperature can therefore be controlled indirectly via the ratio of recycle stream to fresh hydrocarbon feed stream.

A further possible way of controlling the process is to regulate the entry temperature of the hydrocarbon mixture. A lower temperature of the inflowing hydrocarbon mixture leads to better removal of the heat of reaction. On the other hand, the entry temperature of the hydrocarbon mixture can be increased when the catalyst activity decreases so as to achieve a higher reaction rate and thus compensate the decreasing catalyst activity. The entry temperature of the hydrocarbon mixture is generally limited by safety aspects and practical considerations. The maximum entry temperature for a hydrocarbon mixture comprising predominantly butenes and possibly butanes is generally 130° C. When the maximum entry temperature of the hydrocarbon mixture has been reached, the catalyst is exhausted and has to be replaced by fresh catalyst. The exhausted catalyst can, if appropriate, be regenerated.

The oligomerization according to the invention is preferably controlled so that the temperature increase over a catalyst bed is not more than 50° C., in particular not more than 40° C., particularly preferably not more than 30° C. For the present purposes, the temperature increase is the difference between the entry temperature of the hydrocarbon mixture and the exit temperature of the reaction mixture. The adiabatic mode of operation also comprises a process configuration of the process of the invention in which the conversion of the olefins into oligomers is spread over a reactor cascade comprising two or more, preferably two, oligomerization reactors and the partially reacted reaction mixture is cooled after leaving the one reactor and before entering the next reactor of the cascade by means of conventional cooling facilities such as cooling jackets or heat exchangers. In the case of suitable operating conditions, a conversion of from 15 to 50% by weight, based on the olefin content of the hydrocarbon mixture, is achieved per catalyst bed.

The invention is illustrated by the following examples.

EXAMPLES 100 l of a material molded to produce 3*3 mm solid pellets as described in DE 43 39 713 (composition in % by weight: 50% of NiO, 12.5% of $TiO_2$, 33.5% of $SiO_2$, 4% of $Al_2O_3$) served as catalyst in examples 1 and 2 below.

A raffinate II having the following average composition was used in the examples:

| | |
|---|---|
| i-butane: | 5% by weight |
| n-butane: | 18% by weight |
| i-butene: | 2% by weight |
| 1-butene: | 31% by weight |
| trans-2-butene: | 28% by weight |
| cis-2-butene: | 16% by weight |

The experiments were carried out in a reactor cascade comprising two reactors connected in series (diameter: 80 mm, length: 4000 mm, intermediate cooling between the two reactors) with subsequent distillation column. A mixture of raffinate II having the above composition and a recycle stream from the top of the distillation column (after removal of the $C_{8+}$-hydrocarbons) was fed under the reaction conditions to the reactor inlet of the first reactor.

20 l of catalyst was introduced into each of the two reactors and dried at atmospheric pressure and a reactor temperature of 190° C. by passing 100 standard l/l*h of dry $N_2$ (60 ppm moisture content) through the reactors. The course of drying was monitored by means of a humidity measurement (Parametrics) on the gas stream leaving the reactor after cooling to 60° C. After the desired residual moisture content had been reached, the reactor was cooled and the conditioning in the stream of $N_2$ was stopped. The amount of raffinate II and recycle stream (sum of the two constant at 50 kg/h) and also pressure and temperature (average temperature is defined as the average of the respective reactor inlet and reactor outlet temperatures) were set as shown in the following table. The example according to the invention and the comparative example were each carried out using fresh catalyst from the uniform 100 l batch of catalyst.

Table 1 shows the results obtained as a function of the conditioning conditions:

In example I1 according to the invention, a $C_{8+}$ selectivity of 77% and a $C_{12}$ selectivity of 17% were achieved at a butene conversion of 77% and a resulting $C_{8+}$ concentration of 19% at the reactor outlet. The amount of $C_{12}$ produced is 0.22 kg per kg of $C_8$.

Conditions analogous to I1 were set in the comparative example C1. This led, compared to I1, to slightly reduced butene conversions and $C_{8+}$ concentrations at the reactor outlet. The examples C2 and C3 in which the amount of raffinate I1 fed in was reduced or increased in order to obtain a butene conversion comparable to I1 or a $C_{8+}$ concentration comparable to I1 at the reactor outlet were therefore additionally carried out. In comparison with example I1, a $C_8$ selectivity of 81% and a $C_{12}$ selectivity of 14% were achieved in all three comparative examples. The amount of $C_{12}$ produced is 0.17 kg per kg of $C_8$.

The examples show that drying to a residual moisture content of <1000 ppm leads to an increase in the $C_{12}$ selectivity by three percentage points, which based on a given amount of $C_8$ corresponds to a $C_{12}$ capacity increase of 30%. In addition, an increase in activity is also observed.

The invention claimed is:

1. A process for oligomerizing one or more olefins, comprising:
   contacting, in a reactor having an olefin inlet and an oligomer outlet, a gaseous stream comprising one or more $C_2$-$C_8$ olefins with a heterogeneous catalyst consisting essentially of NiO, $SiO_2$ and $TiO_2$, and optionally $Al_2O_3$,
   prior to the contacting, conditioning the catalyst in the reactor by heating at a temperature of greater than 100° C. in an inert gas stream passing through the reactor from the olefin inlet to the oligomer outlet until the inert gas stream in the oligomer outlet has a water content of 1,000 ppm by mass or less,
   wherein contacting the $C_2$-$C_8$-olefins with the heterogeneous catalyst forms an oligomer mixture with a $C_{12}$ selectivity of at least 17% by weight and a conversion of the $C_4$ fraction of the $C_2$-$C_8$ olefins of at least 77% by weight, and
   wherein the activity of the catalyst is greater than the activity obtained when the inert gas stream contains more than 1000 ppm by weight water and the catalyst is used at the same oligomerization conditions.

TABLE 1

Oligomerization conditions and results

| Conditioning | Raffinate II kg/h | Recycle stream kg/h | Average reaction temperature ° C. | Pressure bar | $C_4$ conversion % | $C_{8+}$ conc. at the reactor outlet % | $C_8$ sel. % | Amount of $C_8$ kg/h | $C_{12}$ sel. % | Amount of $C_{12}$ kg/h | $C_{12}/C_8$ kg/kg |
|---|---|---|---|---|---|---|---|---|---|---|---|
| Example 1: According to the invention 36 h drying by means of 100 standard l/l*h of $N_2$, residual moisture content: 400 ppm ||||||||||||
| I1 | 17 | 33 | 60 | 30 | 77 | 19% | 77 | 7.8 | 17 | 1.7 | 0.22 |
| Example 2: Comparison 24 h drying by means of 100 standard l/l*h of $N_2$, residual moisture content: 1600 ppm ||||||||||||
| C1 | 17 | 33 | 58 | 30 | 68 | 17 | 81 | 7.2 | 14 | 1.2 | 0.17 |
| C2 | 14 | 36 | 56 | 30 | 76 | 15 | 81 | 6.6 | 14 | 1.1 | 0.17 |
| C3 | 20 | 30 | 61 | 30 | 65 | 19 | 81 | 8.1 | 14 | 1.4 | 0.17 |

In table 1, the $C_8$ or $C_{12}$ selectivity is defined as the amount of octenes or dodecenes formed divided by the amount of butenes reacted.

2. The process according to claim 1, wherein the outflowing inert gas stream has a water content of less than 500 ppm by weight.

3. The process according to claim 1, wherein the inert gas is nitrogen.

4. The process according to claim 1, wherein the inflowing inert gas stream has a water content of less than 100 ppm by weight.

5. The process according to claim 1, wherein the catalyst is conditioned at a temperature of from 100 to 500° C.

6. The process according to claim 1, wherein the catalyst is conditioned at a pressure of from 0.9 to 1.5 bar.

7. The process according to claim 1, wherein from 50 to 500 standard l/h of inert gas per l of catalyst bed are passed over the catalyst.

8. The process according to claim 1, wherein the olefin comprises n-butene and/or n-pentene.

9. The process according to claim 1, wherein the gaseous stream is brought into contact with the catalyst at a temperature of from 20 to 300° C. and a pressure of from 1 to 100 bar.

10. The process according to claim 1, wherein the catalyst comprises, as significant active constituents, from 10 to 70% by weight of nickel oxide, from 5 to 30% by weight of titanium dioxide and/or zirconium dioxide, from 0 to 20% by weight of aluminum oxide and silicon dioxide as balance.

11. The process according to claim 1, wherein the contacting forms an oligomer mixture having a weight ratio of olefin trimers and higher oligomers formed to olefin dimers of greater than 0.2.

12. The process according to claim 1, wherein contacting the $C_2$-$C_8$-olefin with the heterogeneous catalyst forms an oligomer product such that the concentration of $C_{8+}$ in the oligomer outlet of the reactor is at least 19% by weight.

* * * * *